US012138264B2

(12) United States Patent
Mundhra et al.

(10) Patent No.: US 12,138,264 B2
(45) Date of Patent: *Nov. 12, 2024

(54) PHARMACEUTICAL COMPOSITIONS (71) Applicant: VIIV HEALTHCARE COMPANY, Wilmington, DE (US)

(72) Inventors: Deepak B. Mundhra, Collegeville, PA (US); Rennan Pan, King of Prussia, PA (US)

(73) Assignee: ViiV Healthcare Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/679,621

(22) Filed: May 31, 2024

(65) Prior Publication Data
US 2024/0307387 A1 Sep. 19, 2024

Related U.S. Application Data (63) Continuation of application No. 17/547,682, filed on Dec. 10, 2021, which is a continuation of application No. 15/292,394, filed on Oct. 13, 2016, now Pat. No. 11,224,597, which is a continuation of application No. 13/823,316, filed as application No. PCT/US2011/051713 on Sep. 15, 2011, now abandoned.

(60) Provisional application No. 61/383,541, filed on Sep. 16, 2010.

(51) Int. Cl.
| A61K 31/4985 | (2006.01) |
| A61K 9/16 | (2006.01) |
| A61K 31/505 | (2006.01) |
| A61P 31/00 | (2006.01) |
| A61P 31/18 | (2006.01) |

(52) U.S. Cl.
CPC ............ *A61K 31/4985* (2013.01); *A61K 9/16* (2013.01); *A61K 31/505* (2013.01); *A61P 31/00* (2018.01); *A61P 31/18* (2018.01)

(58) Field of Classification Search
CPC .... A61K 31/4985; A61K 9/16; A61K 31/505; A61P 31/00; A61P 31/18
See application file for complete search history.

(56) References Cited

U.S. PATENT DOCUMENTS

| 3,045,017 | A | * | 7/1962 | Gaudechon | A61K 31/00 540/592 |
| 5,352,459 | A | | 10/1994 | Hollister et al. | |
| 6,077,843 | A | | 6/2000 | Francois et al. | |
| 6,475,491 | B1 | | 11/2002 | Johnson et al. | |
| 6,693,199 | B2 | | 2/2004 | Dressman et al. | |
| 7,842,232 | B2 | | 11/2010 | Bosch et al. | |
| 2005/0084490 | A1 | | 4/2005 | Adams et al. | |
| 2005/0113386 | A1 | * | 5/2005 | Bartoszyk | A61P 25/00 514/254.09 |
| 2007/0041981 | A1 | | 2/2007 | Howard et al. | |
| 2007/0178051 | A1 | | 8/2007 | Pruitt et al. | |
| 2008/0214808 | A1 | | 9/2008 | Spittaels et al. | |
| 2009/0118354 | A1 | | 5/2009 | Liu et al. | |
| 2009/0163519 | A1 | * | 6/2009 | Vermeulen | A61K 9/14 514/259.41 |
| 2009/0297533 | A1 | | 12/2009 | Lichter et al. | |
| 2009/0311237 | A1 | | 12/2009 | Frost | |
| 2009/0318421 | A1 | | 12/2009 | Johns et al. | |
| 2010/0074885 | A1 | | 3/2010 | Schiff et al. | |
| 2010/0189796 | A1 | | 7/2010 | Stokbroekx | |
| 2011/0152303 | A1 | | 6/2011 | Johns | |
| 2011/0275654 | A1 | | 11/2011 | Baert et al. | |

FOREIGN PATENT DOCUMENTS

| JP | 2002255857 A | 9/2002 | |
| RU | 2139280 | 10/1999 | |
| WO | 97/44039 A1 | 11/1997 | |
| WO | 1999002665 A1 | 1/1999 | |
| WO | 2005072706 A2 | 8/2005 | |
| WO | 2006116164 | 11/2006 | |
| WO | WO-2006116764 A1 * | 11/2006 | ......... A61K 31/4985 |
| WO | 2007002832 A1 | 1/2007 | |
| WO | 2007147882 A2 | 12/2007 | |
| WO | 2010011814 A1 | 1/2010 | |
| WO | 2010011815 A1 | 1/2010 | |
| WO | 2010068253 A1 | 6/2010 | |
| WO | 2010068262 A1 | 6/2010 | |
| WO | 2011017395 A1 | 2/2011 | |

OTHER PUBLICATIONS

Affidavit from corresponding Indian application 637/KOLNP/2013, Apr. 26, 2018.
Cohen, et al., Prevention of HIV-1 Infection with Early Antiretroviral Therapy, The New England Journal of Medicine (2011), 365(6):493-505.
Eurasian Patent Search Report dated Dec. 3, 2013, all references cited above.
Baert, L. et al., "Development of a long-acting injectable formulation with nanoparticles of rilpivirine (TMC278) for HIV treatment", European Journal of Pharmaceutics and Biopharmaceutics, Aug. 2009;72(3):502-508.
Affidavit signed by Deepak Mundhra M.S., dated Jan. 29, 2020, from corresponding Indian application 637/KOLNP/2013, Feb. 4, 2020 (Patentee's affidavit).
Mamo, T. et al., "Emerging nanotechnology approaches for HIV/AIDS treatment and prevention," Nanomedicine (Lond.) Feb. 2010; 5(2): 269-285.
15th CROI Conference on Retroviruses and Opportunistic Infections, Boston, MA, Feb. 3-6, 2008.

(Continued)

Primary Examiner — Monica A Shin
(74) Attorney, Agent, or Firm — W. Brett Stauffer (57) ABSTRACT The present Invention relates to pharmaceutical compositions of (3S, 11aR)-N-[(2,4-difluorophenyl)methyl]-2,3,5,7,11,11a-hexahydro-6-hydroxy-3-methyl-5,7-dioxo-oxazolo[3,2-a]pyrido[1,2-d]pyrazine-8-carboxamide, useful in the treatment or prevention of Human Immunodeficiency Virus (HIV) infections.

30 Claims, 4 Drawing Sheets (56) References Cited

OTHER PUBLICATIONS

Non-Final Office Action, U.S. Appl. No. 13/823,316, mailed Mar. 14, 2014.
Final Office Action, U.S. Appl. No. 13/823,316, mailed Oct. 14, 2014.
Non-Final Office Action, U.S. Appl. No. 13/823,316, mailed Jun. 26, 2015.
Final Office Action, U.S. Appl. No. 13/823,316, mailed Apr. 27, 2016.
Non-Final Office Action, U.S. Appl. No. 15/292,394 (issued as U.S. Pat. No. 11,224,597), mailed Jul. 3, 2017.
Final Office Action, U.S. Appl. No. 15/292,394 (issued as U.S. Pat. No. 11,224,597), mailed Jan. 10, 2018.
Non-Final Office Action, U.S. Appl. No. 15/292,394 (issued as U.S. Pat. No. 11,224,597), mailed Sep. 20, 2018.
Final Office Action, U.S. Appl. No. 15/292,394 (issued as U.S. Pat. No. 11,224,597), mailed Jun. 19, 2019.
Non-Final Office Action, U.S. Appl. No. 15/292,394 (issued as U.S. Pat. No. 11,224,597), mailed Apr. 30, 2020.
Non-Final Office Action, U.S. Appl. No. 15/292,394 (issued as U.S. Pat. No. 11,224,597), mailed Nov. 16, 2020.

\* cited by examiner

PHARMACEUTICAL COMPOSITIONS

CROSS-REFERENCE TO RELATED APPLICATIONS

This application is a Continuation of U.S. application Ser. No. 17/547,682 filed Dec. 10, 2021, which is a Continuation of U.S. application Ser. No. 15/292,394 filed Oct. 13, 2016, U.S. Pat. No. 11,224,597, which is a Continuation of U.S. application Ser. No. 13/823,316 filed Mar. 14, 2013, which is a 371 of International Application No. PCT/US2011/051713 filed Sep. 15, 2011, which claims the benefit of U.S. Provisional Application No. 61/383,541 filed Sep. 16, 2010 the disclosures of which are incorporated herein in their entireties.

BACKGROUND OF THE INVENTION

WO 2006/116764 discloses a class of compounds useful in the treatment of HIV infection and AIDS. There is a continuing need for pharmaceutical compositions suitable for treatment over a long period of time. We have discovered pharmaceutical compositions of (3S,11aR)-N-[(2,4-difluorophenyl)methyl]-2,3,5,7,11,11a-hexahydro-6-hydroxy-3-methyl-5,7-dioxo-oxazolo[3,2-a]pyrido[1,2-d]pyrazine-8-carboxamide that are long-acting and therefore suitable for administration to patients in the treatment of HIV infections.

Patient non-compliance is a well known problem accompanying the complex HIV treatment regimens. Patient non-compliance is a critical problem in the treatment of HIV because such non-compliance may lead to the emergence of multiple-drug resistant strains of HIV.

The present invention addresses the issue of non-compliance by formulating (3S,11aR)-N-[(2,4-difluorophenyl)methyl]-2,3,5,7,11,11a-hexahydro-6-hydroxy-3-methyl-5,7-dioxo-oxazolo[3,2-a]pyrido[1,2-d]pyrazine-8-carboxamide as a long-acting parenteral composition suitable for administration, for example, once per month, once every 2 months, once every 3 months, once every 6 months or once every 12 months.

The compositions of the present invention provide for once monthly dosing or longer, thereby addressing the problem of patient non-compliance and pill burden.

SUMMARY OF THE INVENTION

The present Invention relates to pharmaceutical compositions of (3S,11aR)-N-[(2,4-difluorophenyl)methyl]-2,3,5,7,11,11a-hexahydro-6-hydroxy-3-methyl-5,7-dioxo-oxazolo[3,2-a]pyrido[1,2-d]pyrazine-8-carboxamide useful in the treatment or prevention of Human Immunodeficiency Virus (HIV) infections.

DETAILED DESCRIPTION OF THE INVENTION (3S,11aR)-N-[(2,4-difluorophenyl)methyl]-2,3,5,7,11,11a-hexahydro-6-hydroxy-3-methyl-5,7-dioxo-oxazolo[3,2-a]pyrido[1,2-d]pyrazine-8-carboxamide, a compound of formula (I), also referred to as compound (I), has proven antiviral activity against human immunodeficiency virus (HIV).

(I)

The present invention features pharmaceutical compositions comprising the active ingredient (3S,11aR)-N-[(2,4-difluorophenyl)methyl]-2,3,5,7,11,11a-hexahydro-6-hydroxy-3-methyl-5,7-dioxo-oxazolo[3,2-a]pyrido[1,2-d]pyrazine-8-carboxamide, or a pharmaceutically acceptable salt thereof, suitable for administration once monthly or longer.

A further feature of the present invention is a method of using these pharmaceutical compositions.

The present invention features pharmaceutical compositions, comprising (3S,11aR)-N-[(2,4-difluorophenyl)methyl]-2,3,5,7,11,11a-hexahydro-6-hydroxy-3-methyl-5,7-dioxo-oxazolo[3,2-a]pyrido[1,2-d]pyrazine-8-carboxamide, or a pharmaceutically acceptable salt thereof, and a surfactant system.

The present invention features a pharmaceutical composition, comprising a therapeutically effective amount of (3S,11aR)-N-[(2,4-difluorophenyl)methyl]-2,3,5,7,11,11a-hexahydro-6-hydroxy-3-methyl-5,7-dioxo-oxazolo[3,2-a]pyrido[1,2-d]pyrazine-8-carboxamide, or a pharmaceutically acceptable salt thereof, and a surfactant system.

Pharmaceutically acceptable salts include, but are not limited to calcium, magnesium, sodium, or potassium salts and solvates such as hydrates or alcoholates.

The term "therapeutically effective amount," as used herein, means a sufficient amount of a drug, compound, composition, product or pharmaceutical agent to abate or reverse or treat a malady in a human or other mammal.

The present invention features parenteral pharmaceutical compositions for administration to a subject, for example a human.

The present invention features long-acting parenteral pharmaceutical compositions comprising a compound of formula (I) or a pharmaceutically acceptable salt thereof, and a surfactant system for once monthly administration.

The present invention features long-acting parenteral pharmaceutical compositions comprising a compound of formula (I) or a pharmaceutically acceptable salt thereof, and a surfactant system for bi-monthly (once every two months) administration.

The present invention features long-acting parenteral pharmaceutical compositions comprising a compound of formula (I) or a pharmaceutically acceptable salt thereof, and a surfactant system for tri-monthly (once every three months) administration.

The present invention features long-acting parenteral pharmaceutical compositions comprising a compound of formula (I) or a pharmaceutically acceptable salt thereof, and a surfactant system administration once every six or twelve months, or any time point within this range.

The compositions of the present invention provide for the slow release of a compound of formula (I). Therefore, in order to achieve therapeutic levels of drug, a compound of formula (I) advantageously is released from the composition within approximately one to three months, or any time point within this range.

An embodiment of the present invention is a pharmaceutical composition suitable for parenteral administration comprising a compound of formula (I) and a surfactant system comprising a combination of polymers providing for the release of a compound of formula (I) over a period of one to three months. A suitable combination of polymers is, for example, polysorbate 20 and polyethylene glycol (PEG) 3350.

A suitable combination of polymers, namely wetting agent and stabilizer, is required to manufacture a stable suspension. Wetting agents can be selected from a class of non-ionic and anionic surfactants. Representative examples of wetting agents include polyoxyethylene castor oil derivatives, polyoxyethylene sorbitan fatty acid esters (Polysorbate), sorbitan esters of fatty acids (SPAN), Poloxamers, such as LUTROL™ F68, F108 and F127 which are block copolymers of ethylene oxide and propylene oxide, sodium dodecylsulfate and sodium lauryl sulphate.

Representative stabilizers include, but are not limited to, polyethylene glycols, carboxymethylcellulose calcium, carboxymethylcellulose sodium, methylcellulose, hydroxyethylcellulose, hydroxypropylcellulose, hydroxymethylpropylcellulose, polysaccharides, hyarluronic acid, polyvinyl alcohol (PVA) and polyvinylpyrrolidone (PVP).

An example of combination of polymers includes a polysorbate, for example, polysorbate 20 or polysorbate 60 as wetting agent and a polyethylene glycol (PEG), for example, PEG 3350, PEG4000 or PEG8000 as stabilizer.

The present invention features a parenteral pharmaceutical composition comprising a compound of formula (I), or a pharmaceutically acceptable salt thereof, and polysorbate 20 and polyethylene glycol (PEG) 3350.

An embodiment of the present invention is a pharmaceutical composition for parenteral administration comprising a compound of formula (I) and a surfactant system that may be nanomilled to 200 nM.

An embodiment of the present invention is a pharmaceutical composition for parenteral administration comprising a compound of formula (I) and a surfactant system that may be nanomilled to 200 nM in less than 10 hours on a ball mill.

An embodiment of the present invention is a pharmaceutical composition for parenteral administration comprising a compound of formula (I) and a surfactant system that may be size reduced to a mean particle size of 0.1-1.0 μm.

An embodiment of the present invention is a pharmaceutical composition for parenteral administration comprising a compound of formula (I) and a surfactant system that may be size reduced to a mean particle size of 0.1-0.5 μm or 0.2-0.4 μm.

An embodiment of the present invention is a pharmaceutical composition for parenteral administration comprising a compound of formula (I) and a surfactant system that may be size reduced to a mean particle size of 0.1-1.0 μm using wet bead milling.

An embodiment of the present invention is a pharmaceutical composition for parenteral administration comprising a compound of formula (I) and a surfactant system that may be size reduced to a mean particle size of 0.1-1.0 μm using a high pressure milling technology such as microfluidizer or other rotor-stator type of mill or jet mill.

An embodiment of the present invention is a pharmaceutical composition for parenteral administration comprising a compound of formula (I) and a surfactant system suitable for commonly known sterilization technologies such as gamma irradiation, electron beam irradiation and autoclave sterilization.

An embodiment of the present invention is a pharmaceutical composition for parenteral administration comprising a compound of formula (I) and a surfactant system that can be manufactured using aseptic technique.

An embodiment of the present invention is a pharmaceutical composition for parenteral administration comprising a compound of formula (I) and a surfactant system suitable for gamma radiation sterilization.

An embodiment of the present invention is a pharmaceutical composition for parenteral administration comprising a compound of formula (I) and a surfactant system suitable for sterilization technologies by electron beam irradiation or autoclave sterilization.

An embodiment of the present invention is a pharmaceutical composition for parenteral administration that can be presented as a "ready to use" sterile suspension or lyophile for reconstitution.

In general, the pharmaceutical compositions of the present invention comprise 0.1-50% by weight of a compound of formula (I). In general, the pharmaceutical compositions of the present invention comprise 0.1-5% polysorbate 20 as a surfactant and 0.1-5% polyethylene glycol. The pharmaceutical compositions of the present invention may comprise 0.1-10% polysorbate 20 as a surfactant and 0.1-10% polyethylene glycol.

The compositions of the present invention may be administered by subcutaneous or intramuscular injection. The compositions of the present invention may be administered by intradermal or intravitreal injection or implant. The compositions of the present invention may be administered by other parenteral routes of administration.

The preparation of the compositions of the present invention may be performed by milling using a wet bead mill and sterilized by gamma irradiation.

Another feature of the present invention is to simplify treatment regimens for HIV with the goal of enhancing patient compliance by providing a simplified dosage form containing therapeutically effective amounts of a compound of formula (I) or a pharmaceutically acceptable salt thereof.

The present invention also features a method for treating HIV infections in a human, which method comprises administering to said human a composition according to the invention. The present invention features the use of a pharmaceutical composition according to the invention in the treatment of HIV infections. The present invention features the manufacture of a medicament according to the invention for use in medical therapy.

The present invention also features a method for treating HIV infections in a human which method comprises administering to said human a composition according to the invention before, during, or after therapy with a compound of formula (I) in tablet or solution form.

It will be appreciated by those skilled in the art that reference herein to "treatment" extends to treatment of an established malady, infection or symptoms thereof.

The present invention also features a method for preventing HIV infections in a human, which method comprises administering to said human a composition according to the invention. The present invention features the use of a pharmaceutical composition according to the invention in the prevention of HIV infections. The present invention features the manufacture of a medicament according to the invention for use in prophylactic medical therapy.

The present invention also features a method for treating or preventing HIV infections in a human which method comprises administering to said human a composition according to the invention before, during, or after therapy with a compound of formula (I) in tablet or solution form.

Methods for the preparation of a compound of formula (I) are described in WO 2006/116764, WO2010/011814, WO2010/068262, and WO2010/068253 incorporated herein by reference.

The pharmaceutical compositions of the invention are presented as pharmaceutical compositions suitable for parenteral administration. The compositions may also include a safe and effective amount of other active ingredients, such as antimicrobial agents, antiviral agents, or preservatives.

It will be appreciated by those skilled in the art that the amount of active ingredients required for use in treatment will vary according to a variety of factors, including the nature of the condition being treated and the age and condition of the patient, and will ultimately be at the discretion of the attending physician, veterinarian or health care practitioner.

Compositions of the present invention enable patients greater freedom from multiple dosage regimens and ease the needed diligence required in remembering complex daily dosing times and schedules. The compositions of the present invention are particularly suitable for administration as a single dose monthly, bi-monthly or tri-monthly, or at any interval between 30 and 365 days, including every six or twelve months Advantageously, the compositions of the present invention may be administered once per month.

The compositions of the present invention conveniently allow administration in unit dosage form containing, for example, from about 1 mg to about 800 mg, 100 mg to about 800 mg of a compound of formula (I), from about 100 mg to about 600 mg or from about 100 mg to about 400 mg per unit dosage form.

The compositions of the present invention may be used in combination with other pharmaceutical formulations as a component of a multiple drug treatment regimen.

Compositions of the present invention may also be packaged as articles of manufacture comprising a therapeutically effective amount of a compound of formula (I), or a pharmaceutically acceptable salt thereof; and therapeutically effective amount of one or more of the following: nucleoside reverse transcriptase inhibitor, non-nucleoside reverse transcriptase inhibitor, protease inhibitor, integrase inhibitor. An example of a non-nucleoside reverse transcriptase inhibitor is rilpivirine hydrochloride (TMC-278).

The packaging material may also have labelling and information related to the pharmaceutical composition printed thereon. Additionally, an article of manufacture may contain a brochure, report, notice, pamphlet, or leaflet containing product information. This form of pharmaceutical information is referred to in the pharmaceutical industry as a "package insert." A package insert may be attached to or included with a pharmaceutical article of manufacture. The package insert and any article of manufacture labelling provides information relating to the pharmaceutical composition. The information and labelling provides various forms of information utilized by health-care professionals and patients, describing the composition, its dosage and various other parameters required by regulatory agencies such as the United States Food and Drug Agencies.

The present invention further provides the following embodiments:

(a) A parenteral pharmaceutical composition comprising an effective amount of compound of formula (I) or a pharmaceutically acceptable salt thereof, for the long term treatment of HIV infection, or prevention of HIV infection in an individual at risk of being infected by HIV, wherein the composition is administered intermittently at a time interval of at least one week.

(b) The composition according to (a) wherein the composition is administered once every two weeks.

(c) The composition according to (a) wherein the composition is administered once every month.

(d) The composition according to any one of (a) to (c) wherein the effective amount of compound of formula (I) or a pharmaceutically acceptable salt thereof is selected such that the blood plasma concentration of compound of formula (I) in a subject is kept during a prolonged period of time at a level between a maximum blood plasma level which is the blood plasma level that causes significant side effects and the minimum blood plasma level that is the lowest blood plasma level that causes a compound of formula (I) to provide effective treatment or prevention of HIV infection.

(e) The composition according to (d) wherein the blood plasma level of a subject is kept at a level equal to or above about 150 ng/ml, in particular equal to or above about 600 ng/ml.

(f) The composition according to any one of (a) to (e), wherein the composition is administered subcutaneously or intramuscularly.

(g) The composition according to any one of (a) to (f), which comprises the aforementioned surfactant system comprising polysorbate and/or polyethylene glycol.

(h) A method for the treatment or prevention of an HIV infection in a human comprising a pharmaceutical composition according to any of the above (a) to (g).

The dose of a compound of formula (I) administered, which is the amount of compound (I) in the parenteral composition for use in the invention, may be selected such that the blood plasma concentration of compound (I) in a subject is kept during a prolonged period of time above a minimum blood plasma level. The term "minimum blood plasma level" (or $C_{min}$) in this context refers to the lowest efficacious blood plasma level, that is, the blood plasma level of compound (I) that provides effective prevention or treatment HIV infection. In the case of transmission of HIV from an individual infected by HIV to an individual not infected by HIV, this is the lowest blood plasma level that is effective in inhibiting said transmission.

The blood plasma level of compound (1) in a subject may be kept at a level above a minimum blood plasma level of about 170 ng/ml, about 700 ng/ml, or about 1000 ng/ml. The blood plasma levels of compound (I) in a subject may be kept above these minimum blood plasma levels because at lower levels the drug may no longer be effective, thereby increasing the risk of transmission of HIV infection, and may be suboptimal for treatment of HIV infected subjects. Plasma levels of compound (I) may be kept at higher levels to avoid the development of HIV mutations, while maintaining a safety margin.

An advantage of the mode of administration of compound (I) is that high $C_{min}$ levels can be achieved without a commensurate high $C_{max}$, which could mitigate potential side effects associated with $C_{max}$.

The effective amount of compound (I) to be administered may be selected such that the blood plasma concentrations in a subject are kept during a prolonged period of time at a level between a maximum plasma level (or $C_{max}$) and the minimum blood plasma level (or $C_{min}$).

In some embodiments the blood plasma level of compound (I) in a subject may be kept between the minimum blood plasma level (or $C_{min}$ as specified above) and the lower maximum plasma level of compound (1) (or $C_{max}$) which is defined as the level that corresponds to the lowest blood plasma level where compound (I) acts therapeutically. The lowest level where compound (I) acts therapeutically is the lowest blood plasma level that is effective in inhibiting replication of HIV in individuals infected by HIV so that the viral load of HIV is relatively low, for example where the viral load (represented as the number of copies of viral RNA in a specified volume of serum) is below about 200 copies/ml, in particular below about 100 copies/ml, more particularly below 50 copies/ml, specifically below the detection limit of the assay for HIV.

As mentioned above, the blood plasma levels of compound (I) depend on the amount of active ingredient in each parenteral dosage administered. However, it also depends on the frequency of the administrations (i.e. the time interval between each administration). Both parameters can be used to direct the blood plasma levels to the desired values. The dose may be higher where administrations are less frequent.

Although the plasma levels of compound (I) should remain below a maximum or above a minimum value, they may surpass the maximal value or drop below the minimal value during relatively short periods of time, which may be as short as possible. The maximum and minimum plasma levels therefore can be expressed as mean plasma levels during a certain period of time.

In some instances there may be a small initial plasma concentration peak shortly after administration, after which the plasma levels achieve a steady-state.

The dose to be administered may be calculated on a basis of about 1 mg/day to about 50 mg/day, preferably 3 mg/day to about 30 mg/day. This corresponds to a weekly dose of about 7 mg to about 350 mg, preferably about 20 mg to about 200 mg, or to a monthly dose of about 30 mg to about 1500 mg, preferably about 90 mg to about 900 mg. Doses for other dosing regimens can readily be calculated by multiplying the daily dose with the number of days between each administration.

The dose to be administered may be calculated on a basis of about 0.001 mg/kg//day to about 1 mg/kg/day, preferably 0.05 mg/kg/day to about 0.5 mg/kg/day. This corresponds to a weekly dose of about 0.5 mg to about 500 mg, preferably about 20 mg to about 200 mg, or to a monthly dose of about 30 mg to about 1500 mg, preferably about 90 mg to about 900 mg. Doses for other dosing regimens can readily be calculated by multiplying the daily dose with the number of days between each administration.

Once administered, the blood plasma levels of compound (I) in a subject may be more or less stable. After initial rise of the blood plasma levels, a steady state mode may be achieved during a prolonged period of time. By "steady state" is meant the condition in which the amount of drug present in the blood plasma of a subject stays at more or less the same level over a prolonged period of time. The plasma levels of compound (I) may then gradually decrease over time, and when the minimum plasma level is reached, then the next dose of compound (I) may be administered. The term "stays at more or less the same level" does not exclude that there can be small fluctuations of the plasma concentrations within an acceptable range, for example, within about 30%, about 20%, or about 10%. The parenteral compositions of compound (I) may be administered by intravenous injection or, preferably by subcutaneous or intramuscular administration.

The present invention is based on the use of parenteral compositions of the active ingredient compound (I) and therefore the nature of the carrier is selected for suitability for parenteral administration. The carrier in most cases will comprise sterile water, in although other ingredients, for example, to aid solubility, may be included. Injectable solutions or suspensions, for example, may be prepared in which the carrier comprises saline solution, glucose solution or a mixture of saline and glucose solution. Further, the carrier may contain the surfactant system mentioned above such as polysorbate and polyethyleneglycol.

Effect of the Invention

The parenteral pharmaceutical composition comprising compound (I) of the present invention is long-acting. Accordingly, the composition is useful for the treatment or prevention of HIV infection with administration at long time intervals, compared with conventional compositions or with other compounds similar to compound (I) in chemical structure. The compositions of the present invention can be intermittently administered to a patient, e.g., once per week, once per month, once per every 2 months, or one per every 3 months. Therefore, the compositions of the present invention and an administration by subcutaneous (SC) or intramuscular (IM) injection using the same can lead to a remarkable reduction in medication (pill) burden or difficulty in patient compliance. Further, such intermittent administration of a composition of the present invention can contribute to maintaining therapy at appropriate compliance which leads to prevention of emergence of drug resistant HIV and maintaining the efficacy of therapy for an extended period of time.

EXAMPLES

The following examples further describe and demonstrate particular embodiments within the scope of the present Invention. The examples are given solely for illustration and are not to be construed as limitations as many variations are possible without departing from spirit and scope of the Invention.

Example 1: Pharmaceutical Composition

TABLE 1

Composition of a compound of formula (I) Injectable Suspension

| Component | Quantity (mg/mL) | Function |
| --- | --- | --- |
| Compound of Formula (I) | 200.0 | Active |
| Mannitol | 45.0 | Tonicity agent |
| Polysorbate 20 | 20.0 | Wetting agent |
| Polyethylene Glycol (PEG) 3350 | 20.0 | Stabilizer |
| Water for Injection | QS to 1.0 mL | Solvent |

Manufacturing Process

A compound of formula (I), mannitol, polysorbate 20, PEG 3350, and water for injection were compounded and milled using a wet bead mill. The resulting suspension was filled into 3 mL, USP Type I glass vials at a fill volume of 1.5 mL, the vials are stoppered and sealed, and then terminally sterilized by gamma irradiation.

Example 2: Particle Size

A sample of a compound of formula (I) injectable suspension prepared by the process as described in Example 1 was irradiated by gamma irradiation at 29.9-31.5 kGy dose. The milling time was 5 hours. The particle size determined by laser diffraction technique is the following:
X10=75 nm
X50=157 nm
X90=646 nm
X 50 of less than 200 nm was achieved.

Example 3: Gamma Irradiation

A sample of a compound of formula (1) injectable suspension prepared by the process as described in Example 1 was irradiated by gamma irradiation at 29.9-31.5 kGy dose. Samples pre gamma irradiation and post gamma irradiation were tested for drug related impurities by HPLC.

| | Total Drug Related Impurities % area/area |
| --- | --- |
| Pre Gamma Irradiation | 0.19 |
| Post Gamma Irradiation | 0.16 |

The formulation is stable upon gamma irradiation.

Example 4: Manufacturing Process Using High Pressure Microfluidizer

TABLE 2

Composition of a compound of formula (I) Injectable Suspension

| Component | Quantity (mg/mL) | Function |
| --- | --- | --- |
| Compound of Formula (I) | 200.0 | Active |
| Mannitol | 45.0 | Tonicity agent |
| Polysorbate 20 | 20.0 | Wetting agent |
| Polyethylene Glycol (PEG) 3350 | 20.0 | Stabilizer |
| Water for Injection | QS to 1.0 mL | Solvent |

Manufacturing Process

Figure 1:
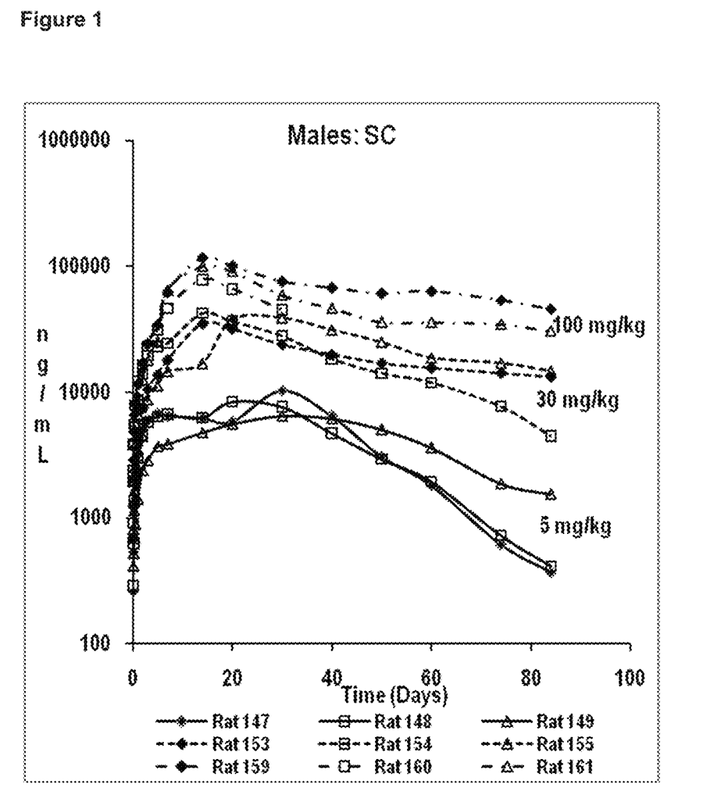
FIG. 1: Plasma Concentration-Time Profiles of a Compound of Formula (I) in Individual Male or Female Rats Following a Single Subcutaneous Injection of a compound of formula (I) Followed by at least a 74-Day Nontreatment Period at a Nominal Dose of 5, 30, or 100 mg/kg.
Figure 2:
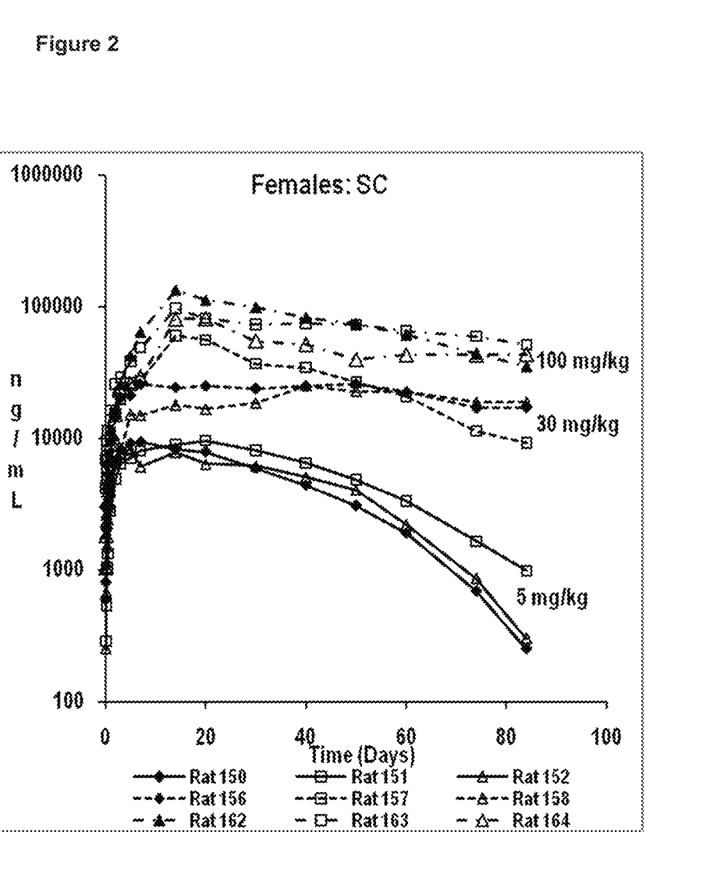
FIG. 2: Plasma Concentration-Time Profiles of a Compound of Formula (1) in Individual Female Rats Following a Single Subcutaneous Injection of a compound of formula (I) Followed by at least a 74-Day Nontreatment Period at a Nominal Dose of 5, 30, or 100 mg/kg.
Figure 3:
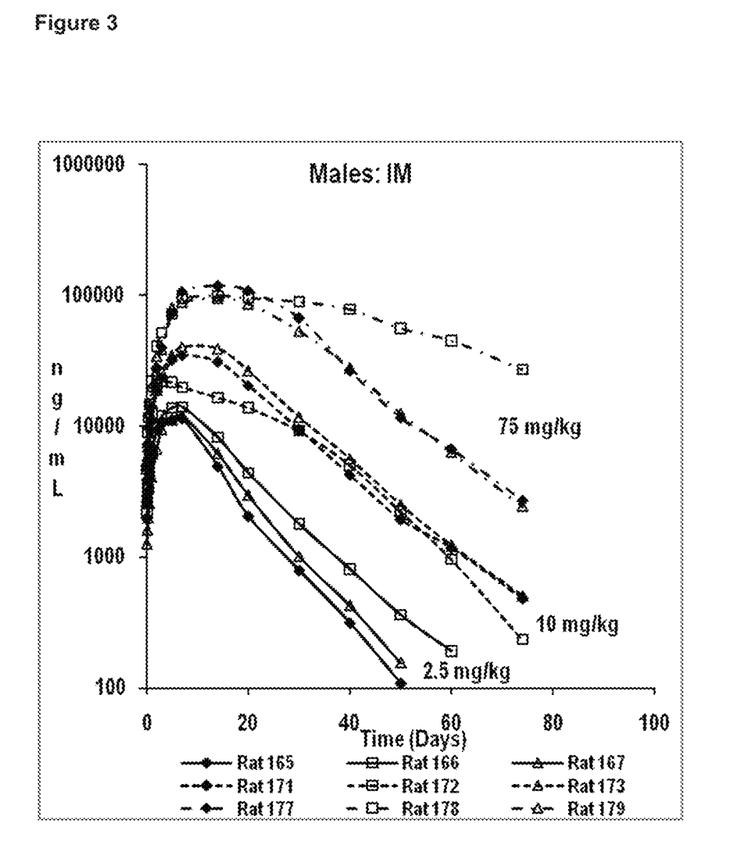
FIG. 3: Plasma Concentration-Time Profiles of a Compound of Formula (I) in Individual Male or Female Rats Following a Single Intramuscular Injection of a compound of formula (I) Followed by at least a 74-Day Nontreatment Period at a Nominal Dose of 2.5, 10, or 75 mg/kg.
Figure 4:
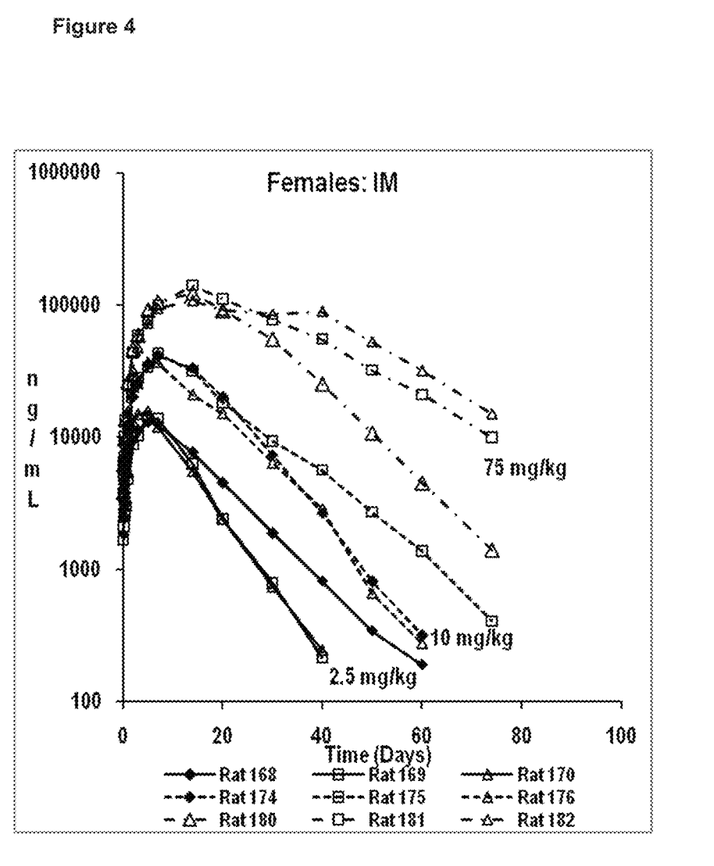
FIG. 4: Plasma Concentration-Time Profiles of a Compound of Formula (I) in individual Female Rats Following a Single Intramuscular Injection of a compound of formula (I) Followed by at least a 74-Day Nontreatment Period at a Nominal Dose of 2.5, 10, or 75 mg/kg.

A compound of formula (I), mannitol, polysorbate 20, PEG 3350, and water for injection were compounded and microfluidized using a Microfluidizer M-110P. The suspension was passed through an interaction chamber (G10Z) with a minimum internal dimension of 87 μm and after 50 pass achieved the particle size as listed below:
X10=82 nm
X50=221 nm
X90=726 nm Example 5: Rat Pharmacokinetics A compound of formula (I) was given once to male and female rats (10/sex/group) at 0 (vehicle), 5, 30, or 100 mg/kg by subcutaneous (SC) injection or 0 (vehicle), 2.5, 10, or 75 mg/kg by intramuscular (IM) injection. After dosing, rats were retained for a 75- to 76-day (SC, including $1^{st}$ 5 control rat/sex) or 84- to 85-day (IM, last 5 control rats/sex; IM) nontreatment period. The vehicle control rats were given both SC and IM injections. FIGS. 1-4 display present plasma concentration-time profiles by route of administration and gender.

The invention claimed is:
1. A parenteral pharmaceutical suspension comprising 0.1-50% by weight a compound of formula (I)

or a pharmaceutically acceptable salt thereof,
0.1-10% by weight polysorbate,
0.1-10% by weight polyethylene glycol 3350, 4000 or 8000,
mannitol, and
water,
wherein, the suspension has mean particle size of 0.1-1 μm, and
wherein the suspension has been sterilized by gamma irradiation.

2. The pharmaceutical suspension according to claim 1 for intramuscular administration.

3. The pharmaceutical suspension according to claim 1 for once per month administration.

4. The pharmaceutical suspension according to claim 1 for administration once every two months.

5. The pharmaceutical suspension according to claim 1 for administration at any interval between 30 and 365 days.

6. The pharmaceutical suspension according to claim 2 for once per month administration.

7. The pharmaceutical suspension according to claim 2 for administration once every two months.

8. The pharmaceutical suspension according to claim 2 for administration at any interval between 30 and 365 days.

9. A method for the treatment of an HIV infection in a human comprising administering the pharmaceutical suspension according to claim 1.

10. A method for the treatment of an HIV infection in a human comprising administering the pharmaceutical suspension according to claim 2.

11. A method for the treatment of an HIV infection in a human comprising administering the pharmaceutical suspension according to claim 6.

12. A method for the treatment of an HIV infection in a human comprising administering the pharmaceutical suspension according to claim 7.

13. A method for the treatment of an HIV infection in a human comprising administering the pharmaceutical suspension according to claim 8.

14. The pharmaceutical suspension according to claim 1, wherein the polysorbate is Polysorbate 20 at a quantity of about 20 mg/mL, and the polyethylene glycol is PEG 3350 at a quantity of 20 mg/mL.

15. The pharmaceutical suspension according to claim 2, wherein the polysorbate is Polysorbate 20 at a quantity of about 20 mg/mL, and the polyethylene glycol is PEG 3350 at a quantity of 20 mg/mL.

16. The pharmaceutical suspension according to claim 6, wherein the polysorbate is Polysorbate 20 at a quantity of about 20 mg/mL, and the polyethylene glycol is PEG 3350 at a quantity of 20 mg/mL.

17. The pharmaceutical suspension according to claim 7, wherein the polysorbate is Polysorbate 20 at a quantity of about 20 mg/mL, and the polyethylene glycol is PEG 3350 at a quantity of 20 mg/mL.

18. The pharmaceutical suspension according to claim 8, wherein the polysorbate is Polysorbate 20 at a quantity of about 20 mg/mL, and the polyethylene glycol is PEG 3350 at a quantity of 20 mg/mL.

19. A method for the treatment of an HIV infection in a human comprising administering the pharmaceutical suspension according to claim 15.

20. A method for the treatment of an HIV infection in a human comprising administering the pharmaceutical suspension according to claim 16.

21. A method for the treatment of an HIV infection in a human comprising administering the pharmaceutical suspension according to claim 17.

22. The pharmaceutical suspension according to claim 1, wherein the pharmaceutical suspension comprises
200 mg/mL compound of formula (I),
20 mg/mL polysorbate 20, and
20 mg/mL PEG 3350.

23. The pharmaceutical suspension according to claim 2, wherein the pharmaceutical suspension comprises
200 mg/mL compound of formula (I),
20 mg/mL polysorbate 20, and
20 mg/mL PEG 3350.

24. The pharmaceutical suspension according to claim 6, wherein the pharmaceutical suspension comprises
200 mg/mL compound of formula (I),
20 mg/mL polysorbate 20, and
20 mg/mL PEG 3350.

25. The pharmaceutical suspension according to claim 7, wherein the pharmaceutical suspension comprises
200 mg/mL compound of formula (I),
20 mg/mL polysorbate 20, and
20 mg/mL PEG 3350.

26. The pharmaceutical suspension according to claim 8, wherein the pharmaceutical suspension comprises
200 mg/mL compound of formula (I),
20 mg/mL polysorbate 20, and
20 mg/mL PEG 3350.

27. A method for the treatment of an HIV infection in a human comprising administering the pharmaceutical suspension according to claim 23.

28. A method for the treatment of an HIV infection in a human comprising administering the pharmaceutical suspension according to claim 24.

29. A method for the treatment of an HIV infection in a human comprising administering the pharmaceutical suspension according to claim 25.

30. A method for the treatment of an HIV infection in a human comprising administering the pharmaceutical suspension according to claim 26.

\* \* \* \* \*